United States Patent
Chang et al.

(10) Patent No.: US 10,564,099 B2
(45) Date of Patent: Feb. 18, 2020

(54) METHOD FOR COMPARATIVE ANALYSIS ON MECHANICAL STRENGTH OF POLYMER MATERIALS

(71) Applicant: Southwest University of Science and Technology, Mianyang (CN)

(72) Inventors: Guanjun Chang, Mianyang (CN); Li Yang, Mianyang (CN); Zhongyuan Lu, Mianyang (CN); Junxiao Yang, Mianyang (CN)

(73) Assignee: Southwest University of Science and Technology, Mianyang, Sichuan Province (CN)

( * ) Notice: Subject to any disclaimer, the term of this patent is extended or adjusted under 35 U.S.C. 154(b) by 0 days.

(21) Appl. No.: 15/883,973

(22) Filed: Jan. 30, 2018

(65) Prior Publication Data

US 2018/0348130 A1    Dec. 6, 2018

(30) Foreign Application Priority Data

Jun. 6, 2017   (CN) .......................... 2017 1 0417181

(51) Int. Cl.
*G01N 21/64*     (2006.01)
*C08G 73/06*     (2006.01)
(Continued)

(52) U.S. Cl.
CPC ..... *G01N 21/6428* (2013.01); *C08G 65/4012* (2013.01); *C08G 65/4056* (2013.01); *C08G 73/0672* (2013.01); *G01N 1/28* (2013.01); *G01N 3/00* (2013.01); *G01N 21/64* (2013.01); *C08G 2650/40* (2013.01); *C08G 2650/50* (2013.01); *C08G 2650/64* (2013.01); *G01N 2021/6432* (2013.01); *G01N 2203/0092* (2013.01)

(58) Field of Classification Search
CPC .................................................. G01N 21/6428
See application file for complete search history.

(56) References Cited

U.S. PATENT DOCUMENTS

| | | | |
|---|---|---|---|
| 2008/0286626 A1* | 11/2008 | Olmeijer | C08G 65/4012 429/483 |
| 2009/0131623 A1* | 5/2009 | Hay | C08G 65/40 528/125 |

\* cited by examiner

*Primary Examiner* — John E Breene
*Assistant Examiner* — Jeffrey C Morgan
(74) *Attorney, Agent, or Firm* — IP Law Leaders PLLC (57) ABSTRACT

A method for detecting or comparing mechanical strength of macro-molecular polymer materials. The detecting method has the steps of measuring the mechanical strength and the maximum value of the fluorescence absorption spectrum of each of the plurality of samples to form a curve relationship or function relationship between the maximum value of the fluorescence absorption spectrum and the mechanical strength; measuring the maximum value of the fluorescence absorption spectrum of the target material, and using the curve relationship or the function relationship to obtain the mechanical strength of the target material. The plurality of samples and the target material are both prepared from a macro-molecular polymer, and the macro-molecular polymer may be composed of disulfonate-difluorobenzophenone, hydroxyindole and difluorobenzophenone as monomers, and the sulfonate groups of the disulfonate-difluorobenzophenone have metal cations. An object of the method is to identify mechanical properties of polymer materials by fluorescence nondestructive detection.

6 Claims, 4 Drawing Sheets

(51) Int. Cl.
*C08G 65/40* (2006.01)
*G01N 1/28* (2006.01)
*G01N 3/00* (2006.01)

METHOD FOR COMPARATIVE ANALYSIS ON MECHANICAL STRENGTH OF POLYMER MATERIALS

CROSS-REFERENCE TO RELATED APPLICATION

The present application claims priority from China Patent Application No. 201710417181.1, filed on Jun. 6, 2017, in the State Intellectual Property Office of P. R. China, the disclosure of which is incorporated herein in its entirety by reference.

TECHNICAL FIELD

One or more embodiments described herein relate to the field of polymer materials detecting, and more particularly, relate to a method for detecting or comparing the mechanical properties of polymer materials having thermosetting properties.

BACKGROUND

High performance polymers have good thermal and mechanical properties, which are widely used in aerospace, microelectronics, precision machinery, medical equipment and other fields, and show great application prospects and huge commercial value. In recent years, with the development of national economy, conventional high-performance polymeric materials are no longer satisfied broader applications, thereby requiring polymer materials to have more superior thermal stability, mechanical strength and anti-cracking properties and the like.

Crosslinking between polymer chains can further improve the performance of high performance polymers, and obtain an ultra-high performance polymer. The thermal stability and mechanical strength of polymers can further be enhanced by chemical crosslinking. In general, the mechanical properties (e.g., stress at break, or tear stress) of polymer materials are substantially detected by a tensile test or the like. However, these conventional detection methods will lead to the damage of the target materials.

SUMMARY

Accordingly, the embodiment is directed to solving at least one of the aforesaid problems of the prior art. For example, one aspect of the embodiment is to provide a method for nondestructive detecting mechanical properties of a polymer material. To achieve the above aspect, the embodiment provides a method for detecting mechanical strength of a polymer material with the following steps of: measuring the mechanical strength and the maximum value of the fluorescence absorption spectrum of each of the plurality of samples to form a curve relationship or function relationship between the maximum value of the fluorescence absorption spectrum and the mechanical strength; and measuring the maximum value of the fluorescence absorption spectrum of the target material, and use the curve relationship or the function relationship to obtain the mechanical strength of the target material, wherein the plurality of samples and the target material are both prepared from a macro-molecular polymer, and the macro-molecular polymer is composed of disulfonate-difluorobenzophenone, hydroxyindole and difluorobenzophenone as monomers, and the sulfonate groups of the disulfonate-difluorobenzophenone have metal cations; or the polymer has a structural formula as shown below:

Specifically, ⊕ represents a metal cation, m is in the range of 1~100, and n is in the range of 200~400.

The metal cation in the aforementioned aspect can be an alkali metal cation. For example, the alkali metal cation can be selected from $K^+$, $Na^+$ and/or $Li^+$, with $K^+$ as the preference. Also, the polymer in the aforementioned aspect can be a cross-linked structure, which is achieved by the interaction between metal cations and π-face of indole groups. In addition, the curve relationship or the function relationship may be a power-law relationship.

According to another aspect of the embodiment, a method for comparing mechanical strength of macro-molecular polymer materials with the following steps of: obtaining first fluorescence maximum value by measuring the maximum value of the fluorescence absorption spectrum of first macro-molecular polymer material; obtaining second fluorescence maximum value by measuring the maximum value of the fluorescence absorption spectrum of second macro-molecular polymer material; and comparing the first fluorescence maximum value with the second fluorescence maximum value, wherein the mechanical strength of the first macro-molecular polymer material is weaker than the second macro-molecular polymer material when the first fluorescence maximum value is greater than the second maximum value, and the mechanical strength of the first macro-molecular polymer material is stronger than the second macro-molecular polymer material when the first fluorescence maximum value is less than the second maximum value, and wherein the first macro-molecular polymer material and the second macro-molecular polymer material are both prepared from macro-molecular polymers, and the macro-molecular polymers are composed of disulfonate-difluorobenzophenone, hydroxyindole and difluorobenzophenone as monomers, and the sulfonate groups of the disulfonate-difluorobenzophenone have metal cations. Or the polymer has a structural formula as shown below:

Specifically, ⊕ represents a metal cation, m is in the range of 1~100, and n is in the range of 200~400.

The metal cation in the above-stated aspect may be an alkali metal cation. For example, the alkali metal cation may be selected from $K^+$, $Na^+$ and/or $Li^+$, with $K^+$ as the preference. Also, the polymer in the above-stated aspect may show a cross-linking structure, which may be achieved by the interaction between metal cations and π-face of indole groups.

Compared to the prior art, the beneficial effects of the embodiment relating to methods of detecting or comparing mechanical strength of macro-molecular polymer materials can detect and identify mechanical properties of macro-molecular polymer materials by fluorescence nondestructive detection.

DETAILED DESCRIPTION

In the following detailed description, a method for comparative analysis on the mechanical strength of macro-molecular polymer materials will be illustrated with reference to the exemplary embodiment and drawings described below.

In an exemplary embodiment, a method for detecting mechanical strength of a macro-molecular polymer material may comprise the following steps of: First, measuring the mechanical strength (e.g., stress at break at break, or tear stress) and the maximum value of the fluorescence absorption spectrum of each of the plurality of samples by conventional methods (e.g., a tensile test). That is, for each sample, obtaining the data pairs of the mechanical strength and the maximum value of the fluorescence absorption spectrum. Subsequently, the curve relationship or the function relationship between the maximum value of the fluorescence absorption spectrum and the mechanical strength can be formed by methods such as drawing or data fitting. For example, the curve relationship or the function relationship may be a power-law relationship.

Second, measure the maximum value of the fluorescence absorption spectrum of the target material, and use the curve relationship or the function relationship to obtain the mechanical strength of the target material. Here, the plurality of samples and the target material are both prepared from macro-molecular polymers. The desired shape and size of the plurality of samples and the target material may be obtained by casting a macro-molecular polymer (e.g., sulfonated poly(Aryl indole Ketone)s, referred to as SPAIKs). For example, the polymer powders can be dissolved in dimethyl sulfoxide (hereinafter referred to as DMSO) and cast onto a slide through a membrane filter, and then the macro-molecular polymer (e.g., sulfonated poly(Aryl indole Ketone)s, referred to as SPAIKs) films are obtained. At room temperature, the resulting films are semi-transparent, non-tacky solids.

The macro-molecular polymer may be composed of disulfonate-difluorobenzophenone, hydroxyindole and difluorobenzophenone as monomers, and the sulfonate groups of the disulfonate-difluorobenzophenone have metal cations. The metal cations can be such as $K^+$, $Na^+$ and/or $Li^+$ and so on. Preferably, the macro-molecular polymer may have crosslinking structures, for example, the crosslinking structures which take the interaction between metal cations and π-face of indole groups as the crosslinking sites.

The preparation of the macro-molecular polymer can be carried out by following ways:

S01, Synthesis of Sulfonated Components

For example, the metal cations react with disulfonate-difluorobenzophenone solution to precipitate sulfonated components. In the sulfonated components, the metal cations of the metal salts can be combined with the sulfonate groups of the disulfonate-difluorobenzophenones. In particular, the metal cations may be derived from metal hydroxides, metal salts, and the like. Metal salts may be alkaline metal salts which are not oxidizable, for example, alkaline chlorides, alkaline carbonates and alkaline nitrates. However, the embodiment is not limited thereto. In addition, disulfonate-difluorobenzophenone solution can be obtained by carrying out a sulfonation reaction of difluorobenzophenone.

Taking sodium cations as an example, the reaction process for the synthesis of the sulfonated components can be as shown in formula (1). Of course, potassium cations can also be used as the cations, the reaction process only need to change Na in formula (1) to K.

S02, Synthesis of SPAIKs

For example, the sulfonated components obtained in the step S01, the hydroxyindoles, and the difluorobenzophenones are mixed in an organic solvent under the protection of inert gas (e.g., nitrogen), and heated to carry out the reaction with stirring to obtain SPAIKs.

In particular, the inert gas may be nitrogen, but the embodiment is not limited thereto. The organic solvent may be dimethyl sulfoxide (DMSO), but the embodiment is not limited thereto, and other organic solvents which may provide a dissolved environment may be used. The temperature of heating is appropriate that the reaction can be carried out without destroying the organic components. For example, the heating temperature may be controlled within the range of 150° C.~200° C., but the embodiment is not limited thereto. In step S02, the ratio of the sulfonated components, the hydroxyindoles, and the difluorobenzophenones can be adjusted as long as SPAIKs can be obtained. For example, in order to improve the utilization of raw materials, the molar ratio of the sulfonated components to the difluorobenzophenones may be 1:(1~10), and the molar ratio of the hydroxyindoles to the difluorobenzophenones may be (1.1~2.0):1, but the embodiment is not limited thereto. Also, the molar ratio of the sulfonated components to the difluorobenzophenones may be 1:(3~7), and the molar ratio of the hydroxyindoles to the difluorobenzophenones may be (1.3~1.7):1.

In addition, after the reaction (e.g., polymerization reaction) in the step S02, cooling, filtration, washing, vacuum drying and the like may be carried out to obtain more pure SPAIKs.

Also, the catalyst may be added to the organic solvent. For example, the catalyst may be one or more selected from the group consisting of potassium carbonate, cesium carbonate, potassium tert-butoxide and sodium tert-butoxide.

Taking sodium cations as an example, the reaction process for the synthesis of the SPAIKs can be as shown in formula (2). Of course, potassium cations can also be used as the cations, the reaction process only need to change Na in formula (2) to K.

The macro-molecular polymer also can be one which has a following structural formula (3), and the chemical name of the polymer is sulfonated poly(Aryl indole Ketone)s (SPAIKs). The macro-molecular polymer represented in formula (3) has crosslinking structures, for example, the crosslinking structures which take the interaction between metal cations and π-face of indole groups as the crosslinking sites.

(3)

Specifically, ⊕ represents a metal cation, the metal cations may be such as $K^+$, $Na^+$ and/or $Li^+$, m is in the range of 1~100, and n is in the range of 200~400.

In another exemplary embodiment, a method for comparing mechanical strength of macro-molecular polymer materials may comprise the following steps of: First, measure the maximum value of the fluorescence absorption spectrum of first macro-molecular polymer material and second macro-molecular polymer material respectively, then the maximum value of the fluorescence absorption spectrum of the first macro-molecular polymer material is referred to as first fluorescence maximum value, and the maximum value of the fluorescence absorption spectrum of the second macro-molecular polymer material is referred to as second fluorescence maximum value.

Second, compare the first fluorescence maximum value with the second fluorescence maximum value, the mechanical strength (e.g., stress at break, or tear stress) of the first macro-molecular polymer material is weaker than the second macro-molecular polymer material when the first fluorescence maximum value is greater than the second maximum value, the mechanical strength (e.g., stress at break, or tear stress) of the first macro-molecular polymer material is stronger than the second macro-molecular polymer material when the first fluorescence maximum value is less than the second maximum value, and the mechanical strength (e.g., stress at break, or tear stress) of the first macro-molecular polymer material is equal to the second macro-molecular polymer material when the first fluorescence maximum value is equal to the second maximum value.

Here, the first macro-molecular polymer material and the second macro-molecular polymer material are both prepared from the macro-molecular polymer. The macro-molecular polymer may be composed of disulfonate-difluorobenzophenone, hydroxyindole and difluorobenzophenone as monomers, and the sulfonate groups of the disulfonate-difluorobenzophenone have metal cations. The metal cations can be such as $K^+$, $Na^+$ and/or $Li^+$. Preferably, the macro-molecular polymer may have crosslinking structures, for example, the crosslinking structures which take the interaction between metal cations and π-face of indole groups as the crosslinking sites.

The other macro-molecular polymer may be a polymer which has a structural as shown in the above formula (3). The macro-molecular polymer shown by formula (3) has crosslinking structures, for example, the crosslinking structures which take the interaction between metal cations and π-face of indole groups as the crosslinking sites.

For convenience of description, the exemplary embodiment has macro-molecular polymer SPAIKs below with m/(m+n)=20%, and metal cation $K^+$ as an example, but the embodiment not limited thereto.

The as-synthesized SPAIKs with m/(m+n)=20% were precipitated in deionized water several times to remove impurity. The purified polymer powders were dissolved in DMSO (10%, w/v). The solution was filtered through a Teflon syringe membrane filter (0.45 μm pore size, Fisher Scientific) and then, casted onto a glass slide. The SPAIKs film with m/(m+n)=20% (referred to as SPAIKs film) was placed in vacuum at 100° C. for 12 h.

An acid-treated SPAIKs film was obtained by immersing the SPAIKs film in sulfuric acid solution at pH=2 for 4 h. During the acid treatment process, the metal cations of the SPAIKs film can be replaced with hydrogen ions, and resulting in a reduction in the number of the crosslinking structures which take the interaction between metal cations and π-face of indole groups as the crosslinking sites. FIG. 1B shows a photograph of the acid-treated SPAIKs film irradiated by UV light at 365 nm in the dark.

Figure 1:
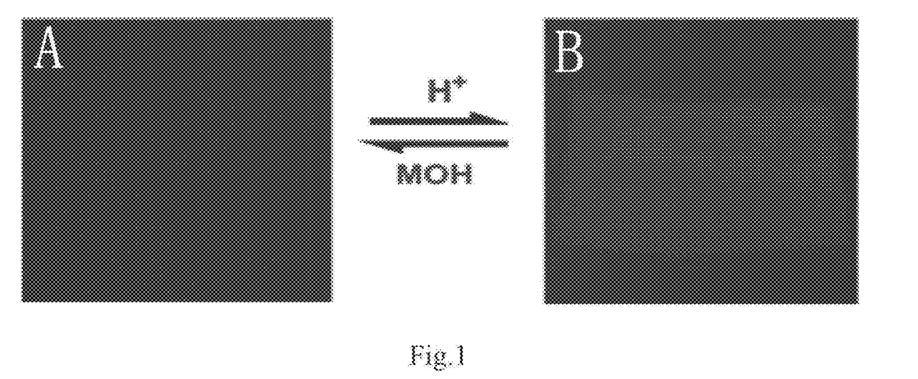
FIG. 1 shows photographs of a sulfonated poly(aryl indole ketone)s film irradiated by UV light at 365 nm in the dark before and after acid treatment.

An alkali-treated SPAIKs film was obtained by immersing the SPAIKs film in a Potassium hydroxide solution at pH=12 for 4 h. During the alkaline treatment process, the metal cations $K^+$ can replace hydrogen ions formed by the acid treatment, and resulting in a recovery in the crosslinking structures which take the interaction between metal cations and π-face of indole groups as the crosslinking sites. The appearance and mechanical properties of the alkali-treated SPAIKs film were almost the same with the original SPAIKs film. FIG. 1A shows a photograph of the alkali-treated SPAIKs film irradiated by UV light at 365 nm in the dark. Referring to FIG. 1, it can be seen that the acid-treated SPAIKs film can emit blue fluorescence under UV light.

Figure 2:
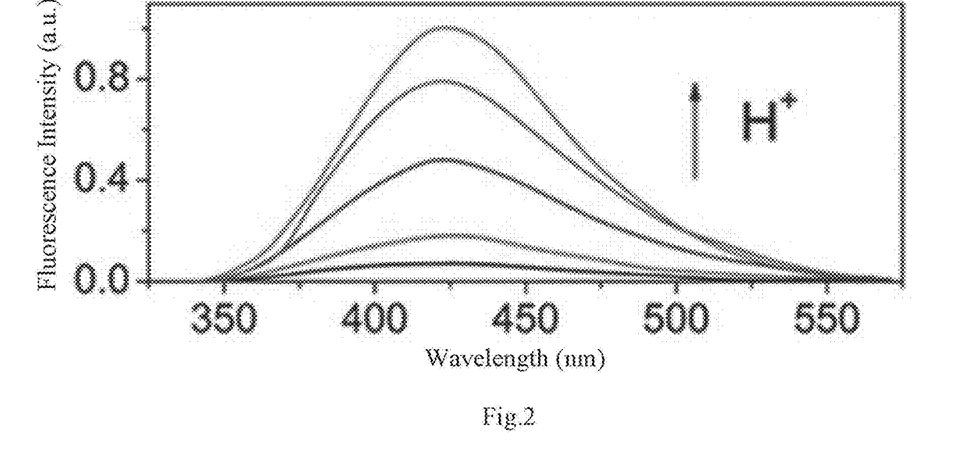
FIG. 2 shows the fluorescence spectra of the sulfonated poly(aryl indole ketone)s film immersed in an acidic solution for varying durations.
Figure 3:
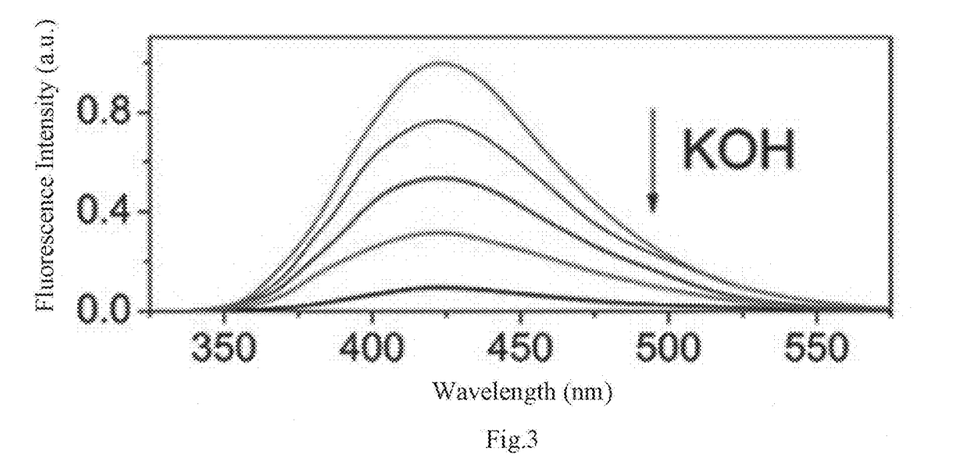
FIG. 3 shows the fluorescence spectra of the sulfonated poly(aryl indole ketone)s film immersed in an alkaline solution for varying durations.

FIG. 2 shows the fluorescence spectra of the SPAIKs film immersed in an acidic solution for varying durations. As shown in FIG. 2, the fluorescence intensity of the SPAIKs film gradually increased with the increase of immersing time. FIG. 3 shows the fluorescence spectra of the SPAIKs film immersed in an alkaline solution for varying durations. As shown in FIG. 3, the fluorescence intensity of the SPAIKs film gradually decreased with the increase of immersing time.

Referring to FIGS. 2 and 3, it can be seen that a change in fluorescence intensity by controlling the immersing time in the acid and the alkaline solutions, and the fluorescence intensity decreases while the crosslinking density increases, the fluorescence intensity increases while the crosslinking density decreases. Herein, the inventors have proposed that the crosslinking and mechanical properties of the SPAIKs film can be nondestructively detected by taking advantage of the fluorescence quenching effect of metal cations to an adjacent conjugated π structure.

Figure 4:
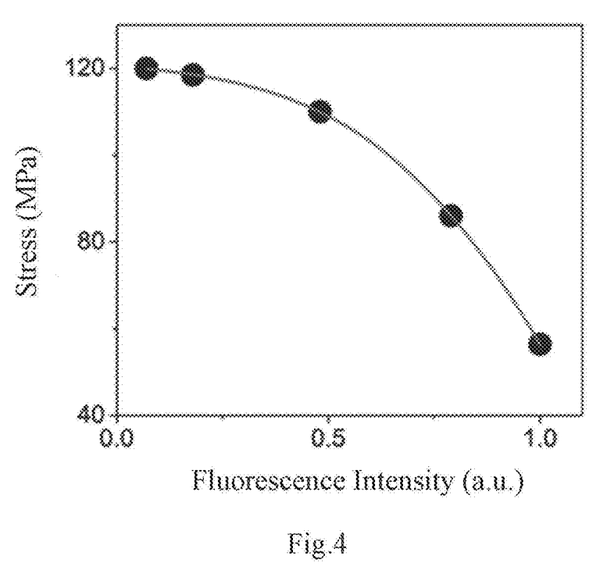
FIG. 4 shows curves between the stress at break and the maximum value of the corresponding fluorescence spectrum of the sulfonated poly(aryl indole ketone)s films in FIG. 2.

FIG. 4 shows curves between the stress at break and the maximum value of the corresponding fluorescence spectrum of each acid-treated SPAIKs film in FIG. 2. The stress at break of was tested for the acid-treated SPAIKs film respectively corresponding to the five curves in FIG. 2, forming the curves of FIG. 4 by taking the stress at break and the maximum value of the fluorescence absorption spectrum of each acid-treated SPAIKs film as data pairs. In other words, a power law relationship between stress at break and the maximum value of the fluorescence absorption spectrum is found by stress-strain experiments for samples at varying immersion durations, indicating that the use of fluorescence could be a nondestructively reporting mechanism for reading out the degree of crosslinking and the mechanical properties.

Figure 5:
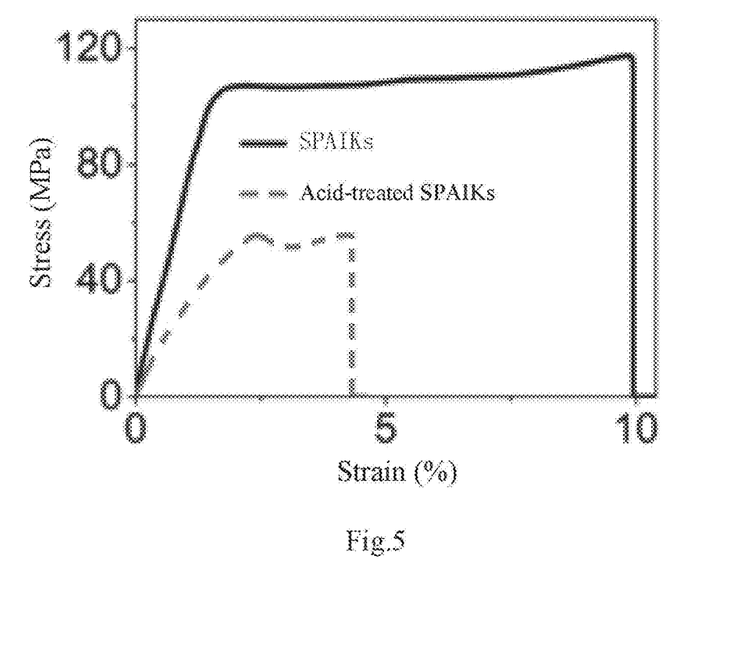
FIG. 5 shows stress-strain curves of the sulfonated poly(aryl indole ketone)s before and after acid treatment.

FIG. 5 shows stress-strain curves of the SPAIKs before and after acid treatment. Referring to FIG. 5, the stress at break of SPAIKs film is about 120 MPa, the strain at break is 10%, and the stress at break of acid-treated SPAIKs film is about 57 MPa, the strain at break is 4.2%. It can be seen that the strong complexation between metal cations and indoles as the crosslinking sites can promote the stability of SPAIKs film and improve its mechanical properties. In other words, when the SPAIKs film based on cation-π interaction was immersing in an acid solution, the metal cations were replaced with protons, that is, the mechanical properties of polymer materials decrease as the cation-π interaction and the crosslinking structures of SPAIKs film disappeared.

Figure 6:
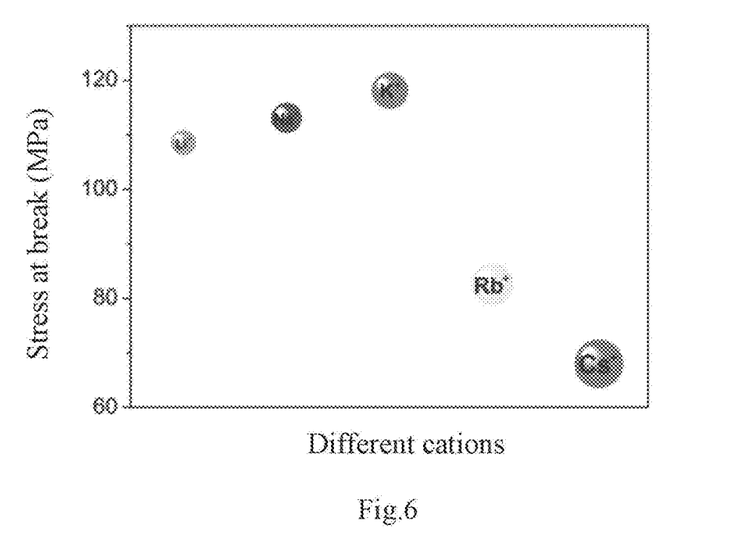
FIG. 6 shows the stress at break of the acid-treated sulfonated poly(aryl indole ketone)s immersed by alkaline solutions with different types of metal cations.

FIG. 6 shows the stress at break of the acid-treated SPAIKs immersed by alkaline solutions with different types of metal cations. As shown in FIG. 6, SPAIKs films with metal cations $K^+$, $Na^+$ or $Li^+$ have better mechanical properties relative to those with metal cations $Rb^+$ or $Cs^+$. This can be interpreted as that protons of the sulfonate groups are replaced by the diffusion of the larger alkaline metal cations, e.g., Rb+ or Cs+, during the process of polymer synthesis. To a large extent, the diffusion of the larger alkali metal cations is hindered, resulting in a reduction in the number of cation-π interactions that act as crosslinking sites, leading to a pronounced decrease in the stress at break. Therefore, in order to obtain better mechanical properties, the metal cations of macro-molecular polymers according to the embodiment are preferably alkaline metal cations, more preferably $K^+$, $Na^+$ and/or $Li^+$.

Above all, the object of the embodiment is to detect and identify mechanical properties of macro-molecular polymer materials by fluorescence nondestructive detection.

This written description uses examples of the subject matter disclosed to enable any person skilled in the art to practice the same, including making and using any devices or systems and performing any incorporated methods. The patentable scope of the subject matter is defined by the claims, and can include other examples that occur to those skilled in the art. Such other examples are intended to be within the scope of the claims. The above-described embodiments are intended to be illustrative in all respects, rather than restrictive, of the embodiments. Thus, the embodiments are capable of many variations in detailed implementation that can be derived from the description contained herein by a person skilled in the art. No element, act, or instruction used in the description of the present application should be construed as critical or essential to the embodiments unless explicitly described as such. Also, as used herein, the article "a" is intended to include one or more items. All United States patents and applications, foreign patents, and publications discussed above are hereby incorporated herein by reference in their entireties.

What is claimed is:

1. A method for detecting mechanical strength of a macro-molecular polymer material, comprising the following steps of:
  measuring the mechanical strength and the maximum value of the fluorescence absorption spectrum of each of the plurality of samples to form a curve relationship or function relationship between the maximum value of the fluorescence absorption spectrum and the mechanical strength;
  measuring the maximum value of the fluorescence absorption spectrum of the target material; and
  using the curve relationship or the function relationship to obtain the mechanical strength of the target material,
  wherein the plurality of samples and the target material are both prepared from a macro-molecular polymer, and the polymer has a structural formula as shown below:

and wherein ⊕ represents a metal cation, m is in the range of 1~100, and n is in the range of 200~400.

2. The method for detecting mechanical strength of a macro-molecular polymer material according to claim 1, wherein the metal cations are alkaline metal cations.

3. The method for detecting mechanical strength of a macro-molecular polymer material according to claim 2, wherein the alkali metal cations are one or more selected from the group consisting of $K^+$, $Na^+$ and $Li^+$.

4. The method for detecting mechanical strength of a macro-molecular polymer material according to claim 1, wherein the macro-molecular polymer has crosslinking structures.

5. The method for detecting mechanical strength of a macro-molecular polymer material according to claim 4, wherein the crosslinking structures are achieved by the interaction between metal cations and π-face of indole groups.

6. The method for detecting mechanical strength of a macro-molecular polymer material according to claim 1, wherein the curve relationship or the function relationship is a power-law relationship.

* * * * *